(12) United States Patent
Takeda et al.

(10) Patent No.: US 11,160,448 B2
(45) Date of Patent: Nov. 2, 2021

(54) OPTICAL MEASUREMENT APPARATUS FOR EYEBALL

(71) Applicant: FUJI BUSINESS INNOVATION CORP., Tokyo (JP)

(72) Inventors: Kazutaka Takeda, Tokyo (JP); Sho Kimura, Tokyo (JP); Taku Kinoshita, Tokyo (JP); Hideaki Ozawa, Tokyo (JP)

(73) Assignee: FUJIFILM BUSINESS INNOVATION CORP., Tokyo (JP)

( * ) Notice: Subject to any disclaimer, the term of this patent is extended or adjusted under 35 U.S.C. 154(b) by 168 days.

(21) Appl. No.: 15/952,247

(22) Filed: Apr. 13, 2018

(65) Prior Publication Data

US 2018/0303333 A1 Oct. 25, 2018

(30) Foreign Application Priority Data

Apr. 21, 2017 (JP) .............................. JP2017-084327

(51) Int. Cl.
| | | |
|---|---|---|
| *A61B 5/1455* | (2006.01) | |
| *A61B 3/00* | (2006.01) | |
| *A61B 3/117* | (2006.01) | |
| *A61B 3/113* | (2006.01) | |
| *A61B 5/145* | (2006.01) | |

(52) U.S. Cl.
CPC ............ *A61B 3/0008* (2013.01); *A61B 3/117* (2013.01); *A61B 3/113* (2013.01); *A61B 5/1455* (2013.01); *A61B 5/14507* (2013.01); *A61B 5/14532* (2013.01); *A61B 2562/0238* (2013.01)

(58) Field of Classification Search
CPC ..... A61B 5/1455; A61B 5/14532; A61B 5/68; A61B 5/6821; A61B 2560/0266
See application file for complete search history.

(56) References Cited

U.S. PATENT DOCUMENTS

| | | | |
|---|---|---|---|
| 6,885,882 B2* | 4/2005 | Cote ................... | A61B 5/14558 600/319 |
| 6,999,808 B2* | 2/2006 | Gobeli ............... | A61B 5/14558 600/316 |
| 9,039,179 B2* | 5/2015 | Brown, Jr. ............. | A61B 3/113 351/208 |
| 9,851,293 B2 | 12/2017 | Takeda et al. | |
| 2011/0105868 A1* | 5/2011 | Westphal ........... | A61B 5/14558 600/319 |
| 2016/0249802 A1 | 9/2016 | Matsushita et al. | |

FOREIGN PATENT DOCUMENTS

| | | |
|---|---|---|
| JP | 2015192861 | 11/2015 |
| JP | 2015194482 | 11/2015 |

\* cited by examiner

*Primary Examiner* — Eric F Winakur
(74) *Attorney, Agent, or Firm* — Volpe Koenig

(57) ABSTRACT

An optical measurement apparatus for an eyeball includes a light emitter, a light receiver, a detector, and a controller. The light emitter emits light such that the light passes across an eyeball of a subject. The light receiver receives the light that has transmitted through the eyeball. The detector detects a direction of the eyeball. The controller performs control such that the light emitter starts emitting light having an intensity used in measurement or the light emitter increases an intensity of light emitted by the light emitter to the intensity used in measurement in a case where the direction of the eyeball detected by the detector is in a predetermined range.

9 Claims, 7 Drawing Sheets

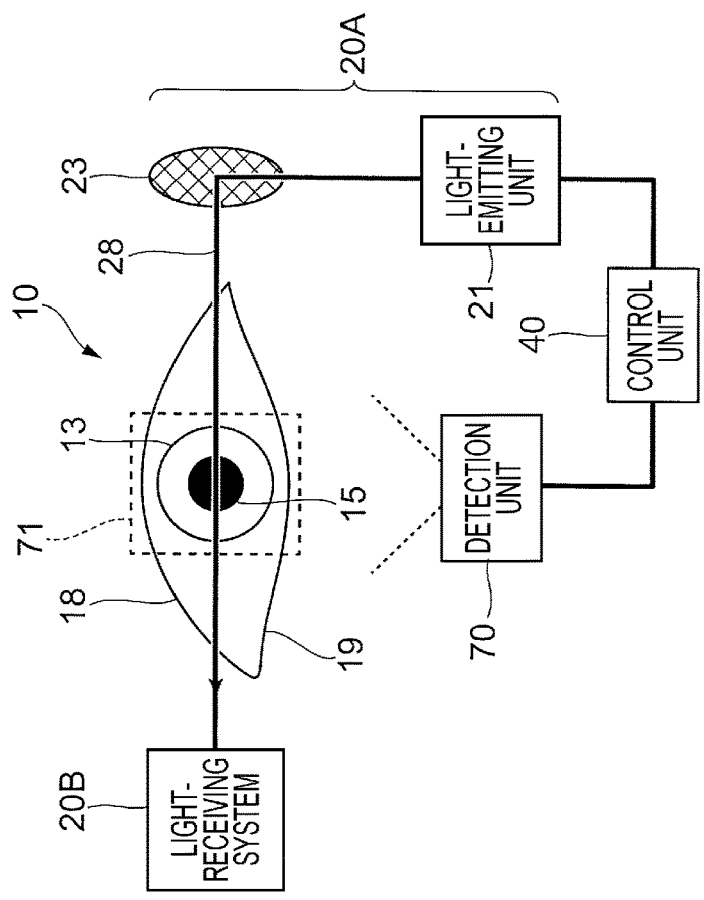
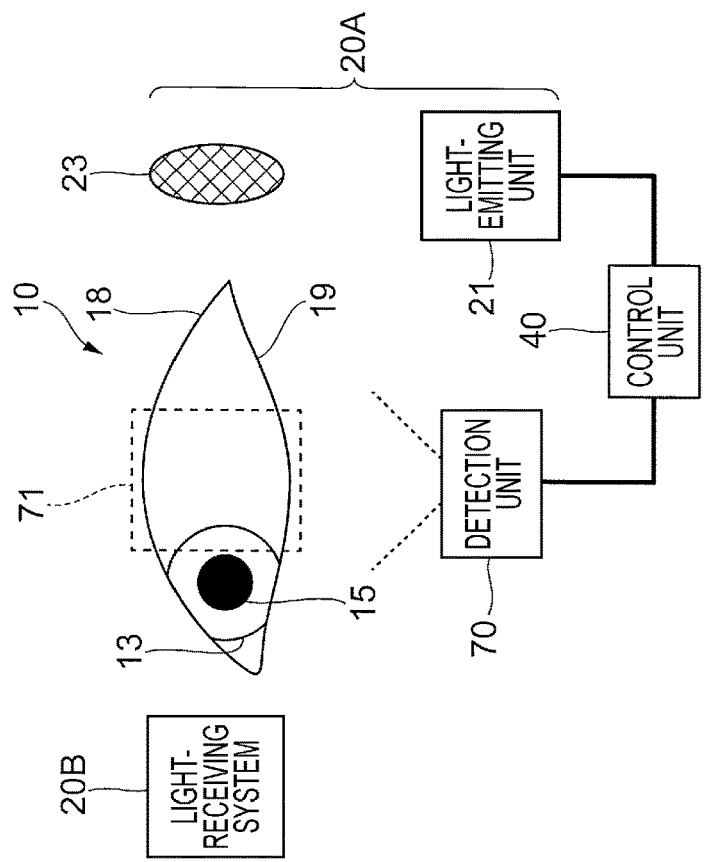
FIG. 5A
FIG. 5B

OPTICAL MEASUREMENT APPARATUS FOR EYEBALL

CROSS-REFERENCE TO RELATED APPLICATIONS

This application is based on and claims priority under 35 USC 119 from Japanese Patent Application No. 2017-084327 filed Apr. 21, 2017.

BACKGROUND

Technical Field

The present invention relates to an optical measurement apparatus for an eyeball.

SUMMARY

According to an aspect of the invention, there is provided an optical measurement apparatus for an eyeball including a light emitter, a light receiver, a detector, and a controller. The light emitter emits light such that the light passes across an eyeball of a subject. The light receiver receives the light that has transmitted through the eyeball. The detector detects a direction of the eyeball. The controller performs control such that the light emitter starts emitting light having an intensity used in measurement or the light emitter increases an intensity of light emitted by the light emitter to the intensity used in measurement in a case where the direction of the eyeball detected by the detector is in a predetermined range.

BRIEF DESCRIPTION OF THE DRAWINGS

An exemplary embodiment of the present invention will be described in detail based on the following figures, wherein:

FIG. 2A is a sectional view taken along a line that extends from the inner corner of the eye toward the outer corner of the eye and is perpendicular to an up-down direction and FIG. 2B is a frontal view of the eyeball;

FIG. 4A illustrates the state in which the direction of the eyeball is in the permission range and FIG. 4B illustrates the state in which the direction of the eyeball is out of the permission range;

FIGS. 5A and 5B illustrate control performed by the control unit when the state in which the direction of the eyeball is out of the permission range changes to the state in which the direction of the eyeball is in the permission range, specifically, FIG. 5A illustrates the state in which the direction of the eyeball is out of the permission range and FIG. 5B illustrates the state in which the direction of the eyeball is in the permission range;

DETAILED DESCRIPTION

An exemplary embodiment of the present invention will be described below with reference to the accompanying drawings.

Optical Measurement Apparatus 1

Figure 1:
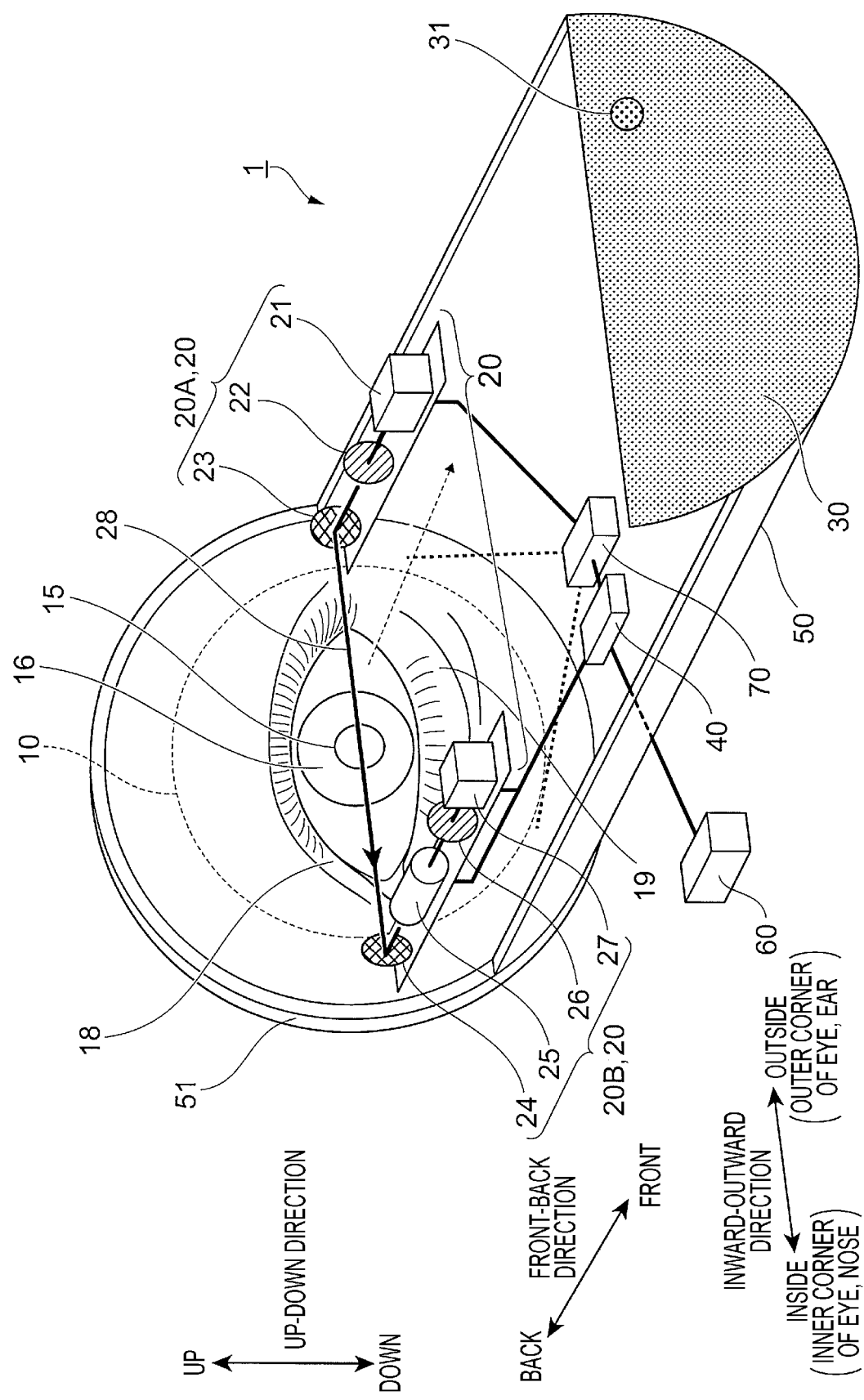
FIG. 1 illustrates an example of a configuration of an optical measurement apparatus according to an exemplary embodiment.

FIG. 1 illustrates an example of a configuration of an optical measurement apparatus 1 according to an exemplary embodiment.

The optical measurement apparatus 1 includes an optical system 20, a display unit 30, a detection unit 70, a control unit 40, a holding unit 50, and a calculation unit 60. The optical system 20 is used to measure the properties of an eyeball 10 of a subject. The display unit 30 displays a marking (line-of-sight target) 31 used to guide the eyeball (line of sight) 10 toward a certain direction. The detection unit 70 detects the direction in which the eyeball 10 is directed (hereinafter, referred to as the direction of the eyeball 10). The control unit 40 controls the optical system 20, the display unit 30, and the detection unit 70. The holding unit 50 holds the optical system 20, the display unit 30, the detection unit 70, and the control unit 40. The calculation unit 60 calculates the properties of the eyeball 10 by using data obtained by measurement performed using the optical system 20.

Note that the control unit 40 is an example of a controller, and the detection unit 70 is an example of a detector.

Hereinafter, the top-bottom direction on the paper is sometimes called an up-down direction of the optical measurement apparatus 1 illustrated in FIG. 1. In addition, the anterior-posterior direction of the subject is sometimes referred to as a front-back direction of the optical measurement apparatus 1. In addition, the medial (or the inner-corner-of-eye side or the nose side)-lateral (the outer-corner-of-eye side or the ear side) direction of the subject is sometimes referred to as an inward-outward direction of the optical measurement apparatus 1.

Examples of the properties of the eyeball 10 measured by the optical measurement apparatus 1 include an angle of rotation (optical rotation $\alpha_M$) of a polarization plane of linear polarization caused by optically active substances contained in the aqueous humor of an anterior chamber (an anterior chamber 13 illustrated in FIG. 2A described later), color absorbance for circular polarization (circular dichroism), and light absorption and light scattering caused by substances contained in the aqueous humor. In addition, the properties of the eyeball 10 also include the properties of a cornea (a cornea 14 illustrated in FIG. 2A described later).

The case of measuring a concentration of an optically active substance contained in the aqueous humor of the anterior chamber by using the angle of rotation (optical rotation $\alpha_M$) of the polarization plane of linear polarization caused by optically active substances will be described below as an example of calculating the properties of the eyeball 10. Herein, the polarization plane of linear polarization indicates a plane along which the electric field oscillates.

FIG. 1 illustrates a pupil 15 of the eyeball 10, an iris 16 surrounding the pupil 15, an upper eyelid 18, and a lower eyelid 19. The pupil 15 of the eyeball 10 is located between the upper eyelid 18 and the lower eyelid 19 and is directed toward the marking (line-of-sight target) 31 displayed on the display unit 30. In FIG. 1, the direction of the eyeball 10 (line of sight) is in the direction toward the marking (line-of-sight target) 31 displayed on the display unit 30. Note that the eyeball 10 illustrated in FIG. 1 is the left eye.

The anterior chamber (the anterior chamber 13 illustrated in FIG. 2A described later) is located on the frontal side of the pupil 15 and the iris 16 and protrudes forward in the eyeball 10 that is substantially spherical. The inside of the anterior chamber is filled with the aqueous humor.

The optical system 20 includes a light-emitting unit 21, a polarizer 22, a first mirror 23, a second mirror 24, a compensator 25, an analyzer 26, and a light-receiving unit 27.

The light-emitting unit 21 includes multiple lasers having different oscillation wavelengths as a light source. Alternatively, the light-emitting unit 21 may include a single laser having a single oscillation wavelength as a light source. In addition, the light-emitting unit 21 may include a light source having a wide wavelength range, such as a light-emitting diode (LED) or a lamp. Light emitted from the light-emitting unit 21 desirably has a narrow wavelength range.

It is assumed herein that the light-emitting unit 21 emits a light beam.

The polarizer 22 is, for example, a Nicol prism. The polarizer 22 allows linearly polarized light on a predetermined polarization plane to pass therethrough out of light entering the polarizer 22.

The first mirror 23 and the second mirror 24 bend an optical path 28 of the light beam. The first mirror 23 and the second mirror 24 desirably maintain linear polarization before and after reflection.

A space for the light-emitting unit 21, the polarizer 22, the compensator 25, the analyzer 26, and the light-receiving unit 27 of the optical system 20 is narrow because of influences of the eyeball 10 having a substantially spherical external shape and the nose (the bridge of the nose) being located on either the side on which the light enters or the side on which transmitted light is received.

Thus, the first mirror 23 and the second mirror 24 are provided in order to set the optical path 28 such that light is caused to enter the eyeball 10 at an angle close to parallel to the eyeball 10 and to transmit across the anterior chamber 13. Specifically, the optical path 28 is bent by using the first mirror 23 and the second mirror 24 for efficient use of the space.

Note that the optical path 28 need not be bent if the optical system 20 is compact enough. In the case where the optical path 28 need not be bent, the optical system 20 need not include the first mirror 23 or/and the second mirror 24.

The compensator 25 is, for example, a magneto-optical element, such as a Faraday element using a garnet or the like. The compensator 25 causes the polarization plane of linear polarization to rotate by using the magnetic field.

The analyzer 26 is a member similar to the polarizer 22. The analyzer 26 allows linearly polarized light on a predetermined polarization plane to pass therethrough.

The light-receiving unit 27 is a light-receiving element, such as a silicon photodiode. The light-receiving unit 27 outputs an output signal corresponding to the intensity of light received thereby.

The light emitted from the light-emitting unit 21 propagates along the optical path 28 and enters the light-receiving unit 27. Specifically, the light emitted from the light-emitting unit 21 toward the eyeball 10 passes through the polarizer 22 and is then bent by the first mirror 23 to a direction crossing the anterior chamber 13 (direction parallel to the eye). Then, the light transmits (passes) across the anterior chamber 13. The light is further bent by the second mirror 24 to a direction away from the eye. The light then passes through the compensator 25 and the analyzer 26 and enters the light-receiving unit 27.

It is assumed that the light-emitting unit 21, the polarizer 22, and the first mirror 23 constitute a light-emitting system 20A, and the second mirror 24, the compensator 25, the analyzer 26, and the light-receiving unit 27 constitute a light-receiving system 20B.

Note that the arranged positions of the light-emitting system 20A and the light-receiving system 20B may be switched.

Note that the light-emitting system 20A including the light-emitting unit 21 is an example of a light emitter, and the light-receiving system 20B including the light-receiving unit 27 is an example of a light receiver. Alternatively, it may be considered that the light-emitting unit 21 is an example of the light emitter and the light-receiving unit 27 is an example of the light receiver.

The display unit 30 displays the marking (line-of-sight target) 31 that is visible to the subject to guide the direction of the eyeball 10 (line of sight). That is, the display unit 30 functions to assist the eyeball 10 to be directed in a desired direction. The display unit 30 also displays the properties of the aqueous humor (such as a concentration of an optically active substance) calculated by the calculation unit 60 after measurement. Note that the display unit 30 need not display the properties of the aqueous humor calculated by the calculation unit 60.

The display unit 30 is an electronic display, such as a liquid crystal display, capable of electronically displaying an image. In this case, the marking (line-of-sight target) 31 is a dot (bright or dark dot) displayed on the electronic display.

Note that the display unit 30 need not be an electronic display. In this case, the marking (line-of-sight target) 31 may be any marking that guides the direction of the eyeball 10 (line of sight) as a result of being viewed. For example, the display unit 30 may be a member including an LED lamp, a marker (marking), a scale, or the like.

The control unit 40 controls the light-emitting unit 21, the compensator 25, and the light-receiving unit 27 of the optical system 20 to obtain measurement data regrading the properties of the eyeball 10 (a concentration of an optically active substance contained in the aqueous humor in this case) and displays the marking (line-of-sight target) 31 on the display unit 30. In addition, the control unit 40 sends the measurement data to the calculation unit 60 and receives a result calculated by the calculation unit 60. Then, the control unit 40 displays the received result on the display unit 30. Further, the control unit 40 receives a signal regarding the direction of the eyeball 10 detected by the detection unit 70 and controls the optical system 20, which will be described in detail later.

The holding unit 50 holds the optical system 20, the display unit 30, the control unit 40, and the detection unit 70. The holding unit 50 holds the optical system 20 such that the optical path 28 set in the optical system 20 passes through the anterior chamber (the anterior chamber 13 illustrated in FIG. 2A described later) in a state in which the one of ends of the holding unit 50 is aligned in contact with a predetermined position near the eyeball 10.

As a method for bringing the holding unit 50 into contact with the predetermined position near the eyeball 10, the subject or another person may hold the optical measurement apparatus 1 with their hand to bring the holding unit 50 into contact with the predetermined position or the holding unit 50 may be brought into contact with the predetermined position by using a driving device that drives the optical measurement apparatus 1 in the front-back direction.

In addition, the region that is in contact with the holding unit 50 need not be near the eyeball 10 as long as the holding unit 50 is aligned with respect to the eyeball 10. That is, the region may be another region of the face of the subject. Further, when the holding unit 50 is successfully aligned without contact, the holding unit 50 need not be brought into contact with the region.

The display unit 30 is disposed on the other end of the holding unit 50.

Note that the optical path 28 is an optical path for which the light emitted from the light-emitting unit 21 transmits across the anterior chamber (the anterior chamber 13 illustrated in FIG. 2A described later) and is received by the light-receiving unit 27 when the eyeball 10 is directed toward the marking (line-of-sight target) 31 displayed on the display unit 30.

The state in which light passes (transmits) across the anterior chamber 13 indicates a state in which the light transmits through the anterior chamber 13 without directly illuminating an unintended portion of the eyeball 10, such as the retina (a retina 17 illustrated in FIG. 2A described later). Examples of the optical path 28 include the cases where the light emitted from the light-emitting unit 21 passes across the anterior chamber 13 from the up side to the down side, passes across the anterior chamber 13 from the down side to the up side, and passes diagonally across the anterior chamber 13 in the front-back direction when the eyeball 10 is viewed from the front as well as the case where the light emitted from the light-emitting unit 21 passes across the anterior chamber 13 in the inward-outward direction as illustrated in FIG. 1. Note that in the cases where the light emitted from the light-emitting unit 21 passes across the anterior chamber 13 from the up side to the down side and from the down side to the up side, the light may transmit in a range less than ±45 degrees with respect to the inward-outward direction.

The holding unit 50 may include an eyepiece member that is processed to fix the optical measurement apparatus 1 with respect to the eyeball 10 and to keep the optical path 28 in place.

The holding unit 50 illustrated in FIG. 1 has a shape obtained by cutting a cylinder at a plane parallel to the axial direction. However, since this shape is adopted to allow the optical system 20 to be viewed easily, the holding unit 50 may have a cylindrical shape. Alternatively, the holding unit 50 may have a tube-like shape whose cross-section is elliptic or quadrangular. Further, a portion of the tube-like shape may be cut off as in FIG. 1.

The calculation unit 60 receives the measurement data from the control unit 40 and calculates the properties of the eyeball 10 (a concentration of an optically active substance contained in the aqueous humor in this case).

The detection unit 70 detects the direction of the eyeball 10. If the line of sight (direction of the eyeball 10) deviates from the marking (line-of-sight target) 31 displayed on the display unit 30, the light may deviate from the optical path 28 that passes across the anterior chamber 13 of the eyeball 10. Consequently, the light may directly illuminate an unintended portion of the eyeball 10, such as the retina 17.

Thus, the detection unit 70 observes the direction of the eyeball 10 and sends a signal regarding the direction of the eyeball 10 to the control unit 40.

A so-called line-of-sight tracking system is usable as the detection unit 70. The line-of-sight tracking system captures an image of the eyeball 10, detects the position of the pupil 15 by performing image processing, and estimates the line of sight. For example, the line-of-sight tracking system captures an image of the eyeball 10 using a charge coupled device (CCD) camera or a complementary metal oxide semiconductor (CMOS) camera that is capable of imaging a visible-light range and that is disposed in front of the face, and estimates the line of sight from positions of the pupil 15 and the iris 16 with respect to the inner corner or outer corner of the eye. Alternatively, the line-of-sight tracking system irradiates the face with near-infrared light, captures an image of the eyeball 10 using a CCD camera or a CMOS camera capable of imaging the visible-light range and an infrared range in this state, and estimates the line of sight from the position of the pupil 15 and the position of the near-infrared light (light source) reflected by the cornea (the cornea 14 illustrated in FIG. 2A described later) (Purkinje image).

Note that the term "line of sight" refers to the direction in which the pupil 15 is directed. If the optical measurement apparatus 1 is aligned at the predetermined position (such as the inner corner or outer corner of the eye) of the face by the holding unit 50, the line of sight is successfully determined by determining the position of the pupil 15. Herein, the term "the direction of the eyeball 10" refers to the direction in which the pupil 15 is directed and is synonymous to the line of sight.

Hereinafter, the line of sight is sometimes referred to as the direction of the eyeball 10.

Note that the positions of the inner corner or outer corner of the eye, the pupil 15, the iris 16, and the Purkinje image may be extracted by performing image processing, such as binary processing, on the captured image of the eyeball 10.

Accordingly, the control unit 40 sets a predetermined range (a permission range 71 illustrated in FIGS. 4A and 4B described later) in the image of the eyeball 10 located between the upper eyelid 18 and the lower eyelid 19 and determines whether the pupil 15 detected by the detection unit 70 is in the predetermined range (the permission range 71).

If the pupil 15 of the eyeball 10 is in the predetermined range (the permission range 71), the light emitted from the light-emitting unit 21 transmits across the anterior chamber 13 of the eyeball 10 without directly reaching the retina 17 of the eyeball 10.

Note that the detection unit 70 may detect the direction of the eyeball 10 by using a method other than the line-of-sight tracking system described above.

In addition, the detection unit 70 is placed at a position below the eyeball 10. However, the detection unit 70 may be placed in front of the eyeball 10, at a position above the eyeball 10, a position on the inward side of the eyeball 10, or the outward side of the eyeball 10, for example.

Eyeball 10 and Optical Path 28

Figure 2A:
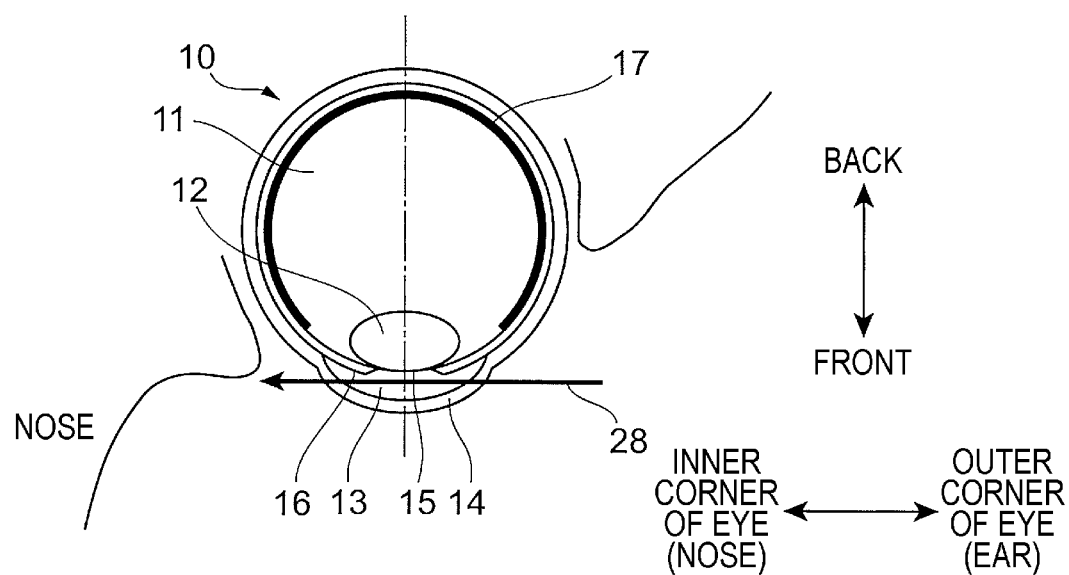
FIGS. 2A and 2B illustrate an optical path that passes across an eyeball and an anterior chamber of the eyeball, specifically.
Figure 2B:
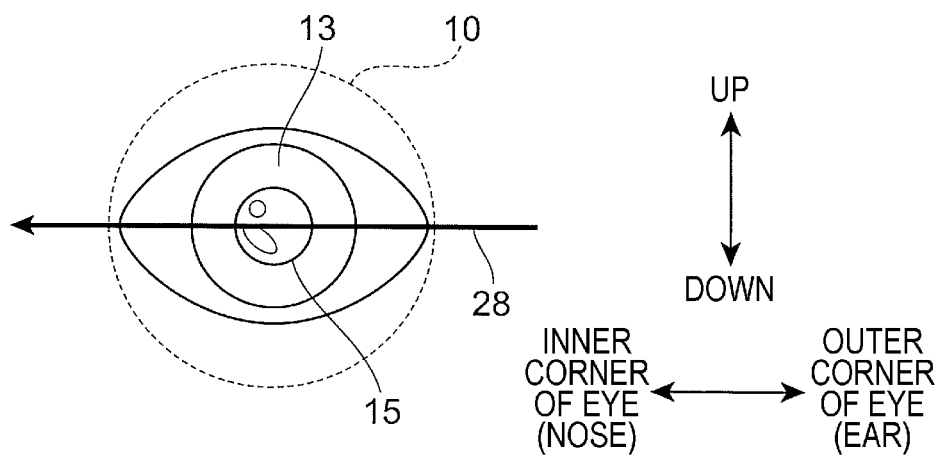

FIGS. 2A and 2B illustrate the optical path 28 that passes across the eyeball 10 and the anterior chamber 13 of the eyeball 10. Specifically, FIG. 2A is a cross-sectional view taken along a line that extends from the inner corner toward the outer corner of the eyeball 10 and is perpendicular to the up-down direction, and FIG. 2B is a frontal view of the eyeball 10.

As illustrated in FIG. 2A, the external shape of the eyeball 10 is substantially spherical. A vitreous body 11 is located substantially at the center of the eyeball 10. A crystalline lens 12 serving as a lens is buried in a portion of the vitreous body 11. The anterior chamber 13 is located on the outer side of the crystalline lens 12, and the cornea 14 is located on the outer side of the anterior chamber 13. The peripheral portion of the crystalline lens 12 is surrounded by the iris 16. The pupil 15 is located substantially at the center of the iris 16. The vitreous body 11 is covered with the retina 17 except for the portion that is in contact with the crystalline lens 12.

That is, the anterior chamber 13 is a region surrounded by the cornea 14 and the crystalline lens 12 and protrudes in a convex manner from the spherical eyeball 10. The anterior chamber 13 is filled with the aqueous humor.

In this example, the optical path 28 is set to extend from the outer corner of the eye (ear side) toward the inner corner of the eye (nose side).

As illustrated in the frontal view of the eyeball 10 in FIG. 2B, the optical path 28 that passes through the anterior chamber 13 has the longest optical path length when the optical path 28 is located in front of the pupil 15.

Note that the light that propagates along the optical path 28 is a light beam.

Now, the case of measuring a concentration of glucose (glucose concentration), which is an optically active substance contained in the aqueous humor, by using an angle of rotation (optical rotation $\alpha_M$) of the polarization plane of linear polarization caused by optically active substances contained the aqueous humor will be described as an example of calculating the properties of the aqueous humor by using the optical measurement apparatus 1.

An amount of insulin to be administered to diabetes patients is controlled in accordance with the glucose concentration in the blood. Thus, diabetes patients are required to grasp the glucose concentration in the blood. A major method for measuring the glucose concentration in the blood is that the patient pricks the fingertip or the like with a syringe to sample a small amount of blood. However, even sampling of a small amount of blood involves pain. Thus, there is an increasing demand for a non-invasive testing method that replaces an invasive testing method, such as pricking.

The aqueous humor of the anterior chamber 13 of the eyeball 10 contains substantially the same components as those of the serum. Specifically, the aqueous humor contains protein, glucose, ascorbic acid, etc. It is also known that the glucose concentration in the blood and the glucose concentration in the aqueous humor have a correlation. Further, since the aqueous humor does not contain blood cell substances, an influence of light scattering is small. The protein, glucose, ascorbic acid, etc. contained in the aqueous humor are optically active substances and have a property of causing optical rotation. That is, the aqueous humor is useful as a portion in which the glucose concentration or the like is measured optically by using optical rotation. If the glucose concentration is successfully measured optically, such a method is a non-invasive testing method.

Examples of the optical path that is settable in a method for optically determining a concentration of an optically active substance contained in the aqueous humor include an optical path for which light enters the eyeball 10 at an angle close to the right angle in addition to the above-described optical path 28 that passes across the anterior chamber 13 of the eyeball 10.

With the optical path for which light enters the eyeball 10 at an angle close to the right angle, the light is reflected by an interface between the aqueous humor of the anterior chamber 13 and the iris 16 or an interface between the aqueous humor and the crystalline lens 12 and the reflected light is received. When this optical path is used, the retina 17 may be directly illuminated by the light. In particular, when a laser having high coherence and high energy density is used in the light-emitting unit 21, the retina 17 may receive an undesirable influence depending on the duration of light illumination if the retina 17 is directly illuminated by the light.

In contrast, with the optical path 28 that passes across the anterior chamber 13 of the eyeball 10, direct illumination of an unintended portion of the eyeball 10, such as the retina 17, by the light is suppressed.

Note that the state of direct illumination indicates a state in which light having an intensity used in measurement enters the eyeball 10 and reaches an unintended portion of the eyeball 10, such as the retina 17, without a large decrease in the intensity. In other words, the state of direct illumination indicates a state in which a light beam that has entered the eyeball 10 reaches an unintended portion of the eyeball 10, such as the retina 17, while receiving an influence of refraction caused by the cornea 14 or the like but without a large decrease in the intensity. That is, direct illumination light excludes weak light having an intensity that does not cause an undesirable influence, scattered light caused by a substance in the eyeball 10, and reflected light caused by a portion or member having a small reflectance located inside or outside the eyeball 10.

Figure 3:
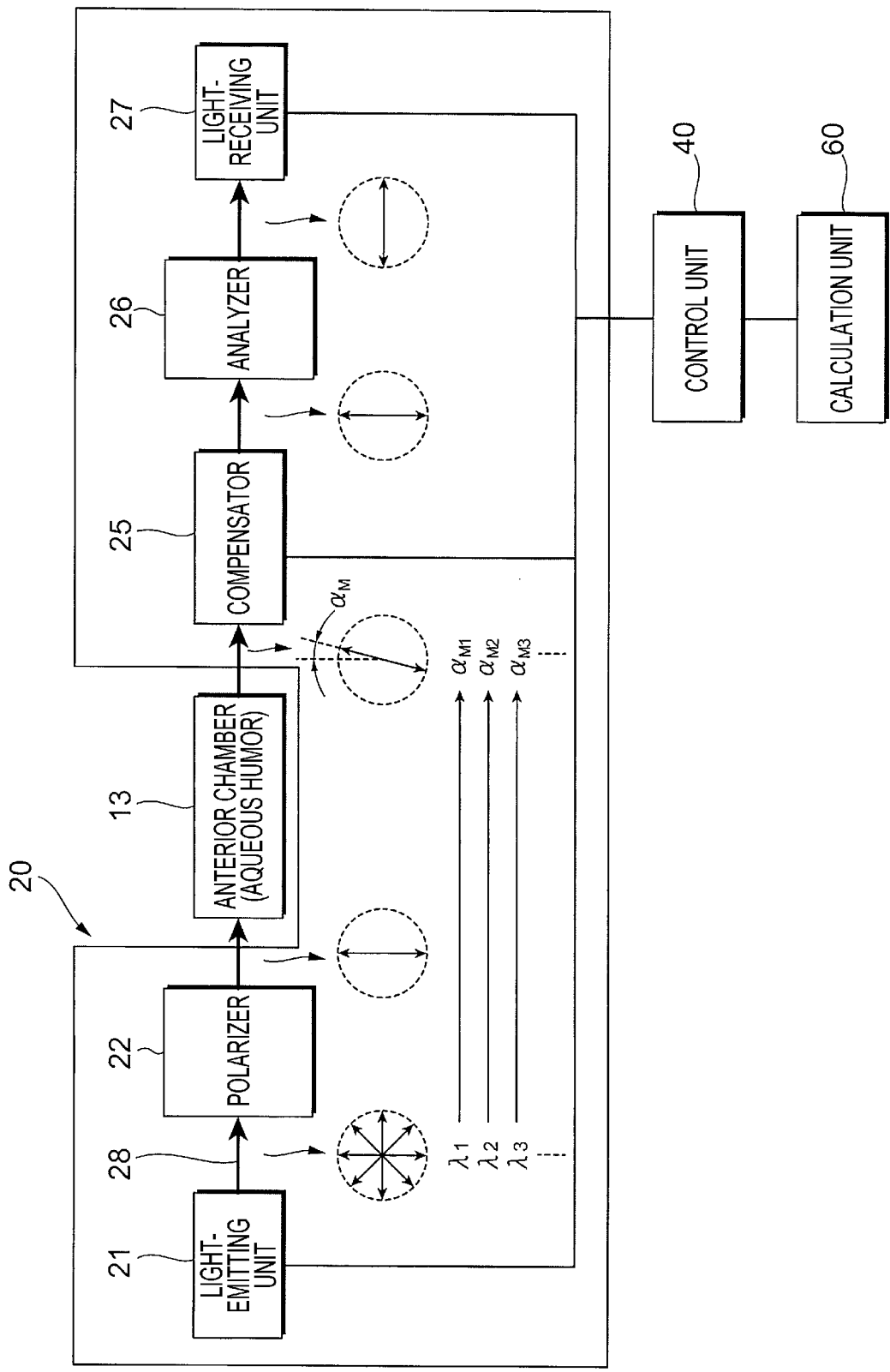
FIG. 3 illustrates a method for measuring an angle of rotation (optical rotation) of a polarization plane caused by optically active substances contained in aqueous humor of the anterior chamber by using the optical measurement apparatus.

FIG. 3 illustrates a method for measuring an angle of rotation (optical rotation) of the polarization plane caused by optically active substances contained in the aqueous humor of the anterior chamber 13 by using the optical measurement apparatus 1. For ease of explanation, it is assumed that the optical path 28 is not bent (is linear). Thus, illustration of the first mirror 23 and the second mirror 24 is omitted.

In the optical system 20 illustrated in FIG. 3, the polarization state viewed from the traveling direction of the light is illustrated by using an arrow in each circle between the light-emitting unit 21, the polarizer 22, the anterior chamber 13, the compensator 25, the analyzer 26, and the light-receiving unit 27.

It is assumed that the light-emitting unit 21 emits light having random polarization planes. Then, the polarizer 22 allows linearly polarized light on a predetermined polarization plane to pass therethrough. In FIG. 3, linearly polarized light on a polarization plane parallel to the paper surface passes through the polarizer 22 as an example.

The polarization plane of the linearly polarized light that has passed through the polarizer 22 rotates due to optically active substances contained in the aqueous humor of the anterior chamber 13. It is assumed in FIG. 3 that the polarization plane rotates at an angle $\alpha_M$ (optical rotation $\alpha_M$).

Then, a magnetic field is applied to the compensator 25 to return the polarization plane that has rotated due to the optically active substances contained in the aqueous humor of the anterior chamber 13 back to the original state.

Then, the linearly polarized light that has passed through the analyzer 26 is received by the light-receiving unit 27. The light-receiving unit 27 converts the light into an output signal corresponding to the intensity of the light.

Now, an example of a method for measuring the optical rotation $\alpha_M$ by using the optical system 20 will be described.

First, the compensator 25 and the analyzer 26 in the optical system 20 including the light-emitting unit 21, the polarizer 22, the compensator 25, the analyzer 26, and the light-receiving unit 27 are configured in a state in which light emitted by the light-emitting unit 21 does not transmit through the anterior chamber 13, such that the output signal of the light-receiving unit 27 has the smallest value. As illustrated in FIG. 3, the polarization plane of linearly polarized light that has passed through the polarizer 22 is perpendicular to the polarization plane of the linearly polarized light that passes through the analyzer 26 in the state in which the light does not transmit through the anterior chamber 13.

Note that it is assumed in FIG. 3 that both the polarization plane of the polarizer 22 and the polarization plane of the linearly polarized light that is to pass through the analyzer 26 are parallel to the paper surface. However, in the case where the polarization plane is rotated in advance by the compensator 25, the polarization plane of linearly polarized light that is to pass through the analyzer 26 may be inclined from the plane parallel to the paper surface. That is, the compensator 25 and the analyzer 26 just need to be set such that the output signal of the light-receiving unit 27 has the smallest value in the state in which the light does not transmit through the aqueous humor of the anterior chamber 13.

Then, the light is configured to transmit through the anterior chamber 13. In this case, the polarization plane rotates due to optically active substances contained in the aqueous humor of the anterior chamber 13. The value of the output signal of the light-receiving unit 27 consequently deviates from the smallest value. Thus, the magnetic field applied to the compensator 25 is set such that the output signal of the light-receiving unit 27 has the smallest value. That is, the polarization plane is rotated by the compensator 25 to be perpendicular to the polarization plane of the linearly polarized light that passes through the analyzer 26.

Thus, the angle by which the polarization plane is rotated by the compensator 25 corresponds to the optical rotation $\alpha_M$ caused by optically active substances contained in the aqueous humor. Since a relationship between the magnitude of the magnetic field applied to the compensator 25 and the angle by which the polarization plane is rotated is known in advance, the optical rotation $\alpha_M$ is determined from the magnitude of the magnetic field applied to the compensator 25.

Although an example of using the compensator 25 is described as the method for determining the optical rotation $\alpha_M$, the optical rotation $\alpha_M$ may be determined without using the compensator 25. In addition, although FIGS. 1 and 3 illustrate the crossed Nicols method (using the compensator 25) that is the most fundamental measurement method for measuring the angle of rotation (optical rotation $\alpha_M$) of the polarization plane, any of other measurement methods such as a rotating analyzer method, a Faraday modulation method, and an optical delay modulation method may be used.

More specifically, multiple light beams having respective wavelengths $\lambda$ (wavelengths $\lambda_1, \lambda_2, \lambda_3, \ldots$) are emitted to the aqueous humor of the anterior chamber 13 from the light-emitting unit 21, and the optical rotations $\alpha_M$ (optical rotations $\alpha_{M1}, \alpha_{M2}, \alpha_{M3}, \ldots$) are determined for the respective wavelengths $\lambda$. The calculation unit 60 receives the pairs of the wavelength $\lambda$ and the optical rotation $\alpha_M$ and calculates a concentration of a target optically active substance.

As described above, the aqueous humor contains multiple optically active substances. Thus, each of the calculated optical rotations $\alpha_M$ is the sum of optical rotations $\alpha$ caused by the respective optically active substances. Thus, the concentration of the target optically active substance needs to be calculated from the measured optical rotations $\alpha_M$.

Since a known method is usable to calculate the concentration of the target optically active substance, a description thereof is omitted.

Control by Control Unit 40 in Accordance with Direction of Eyeball 10 Detected by Detection Unit 70

Figure 4A:
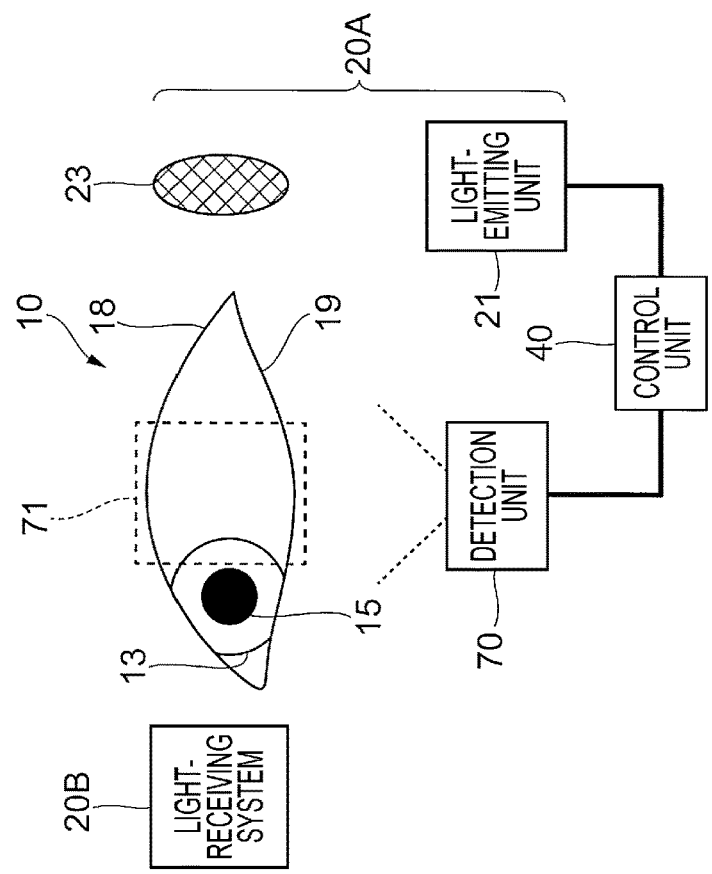
FIGS. 4A and 4B illustrate control performed by a control unit in states in which the direction of the eyeball is in a permission range and out of the permission range, specifically.
Figure 4B:
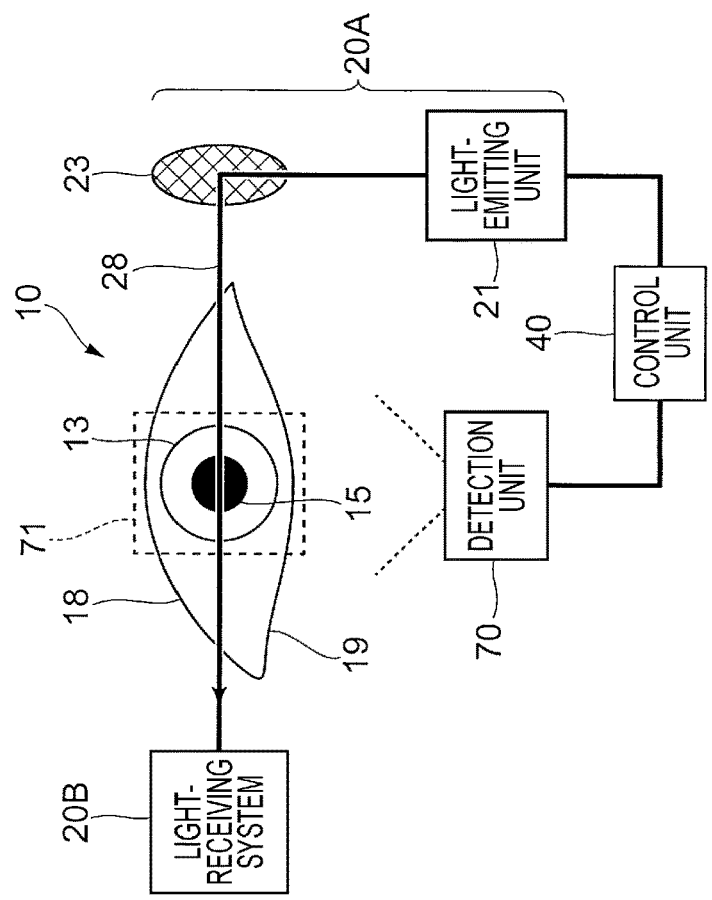

FIGS. 4A and 4B illustrate control performed by the control unit 40 in states in which the direction of the eyeball 10 is in and out of the permission range 71. Specifically, FIG. 4A illustrates the state in which the direction of the eyeball 10 is in the permission range 71, and FIG. 4B illustrates the state in which the direction of the eyeball 10 is out of the permission range 71. Note that the state in which the direction of the eyeball 10 is out of the permission range 71 indicates the state in which the direction of the eyeball 10 is not in the permission range 71.

Illustration of the optical system 20 is simplified in FIGS. 4A and 4B. That is, the light-emitting unit 21 and the first mirror 23 illustrated in FIG. 1 are illustrated as the light-emitting system 20A. In addition, the components of the light-receiving system 20B are collectively illustrated as the light-receiving system 20B.

The permission range 71 illustrated in FIGS. 4A and 4B is defined as follows. If the direction of the eyeball 10 is in this range, light emitted from the light-emitting unit 21 passes across the anterior chamber 13 of the eyeball 10 without directly reaching an unintended portion of the eyeball 10, such as the retina 17 of the eyeball 10. If the direction of the eyeball 10 is out of this range, the light emitted from the light-emitting unit 21 may directly reach an unintended portion of the eyeball 10, such as the retina 17 of the eyeball 10.

Herein, this range is referred to as the permission range 71 because the light-emitting unit 21 is permitted to start emitting light having an intensity used in measurement or to increase the intensity of the light to the intensity used in measurement when the direction of the eyeball 10 is in this range.

Note that it is sufficient to suppress a situation where the light having the intensity used in measurement directly reaches an unintended portion of the eyeball 10, such as the retina 17, when the direction of the eyeball 10 is out of this range. That is, when the light emitted from the light-emitting unit 21 has an intensity that does not cause any undesirable influence even if the light reaches an unintended portion of the eyeball 10, such as the retina 17, in the state in which the direction of the eyeball 10 is out of this range, such light may reach the unintended portion of the eyeball 10. Thus, control may be performed to increase/decrease the intensity of the light emitted by the light-emitting unit 21 as well as to start/stop (including prohibit) emission of the light.

Herein, the state in which the direction of the eyeball 10 is in the permission range 71 indicates a state in which the center of the pupil 15 is in the permission range 71. In addition, the state in which the direction of the eyeball 10 is out of the permission range 71 indicates a state in which the center of the pupil 15 is out of the permission range 71. The permission range 71 may be set based on whether the pupil 15, instead of the center of the pupil 15, is in the permission range 71. That is, the detection unit 70 detects the direction of the eyeball 10 from the position of the pupil 15.

Note that the direction of the eyeball 10 may be detected using, for example, a Purkinje image other than the pupil 15.

The permission range 71 may be set in advance by using weak light having an intensity that does not cause any undesirably influence even if an unintended portion of the eyeball 10, such as the retina 17, is illuminated with the light or by using guide light used in optical path setting (light that is weak, has a wavelength different from that of measurement light, and is easily visible). That is, the permission range 71 is a predetermined range.

It is assumed herein that the permission range 71 is a quadrangular range as indicated by a dash line in FIGS. 4A and 4B. However, the permission range 71 just needs to be a range for which the measurement light passes across the anterior chamber 13 of the eyeball 10 without directly reaching an unintended portion of the eyeball 10, such as the retina 17 of the eyeball 10, and may have another shape.

When the direction of the eyeball 10 (the pupil 15) is in the permission range 71 as illustrated in FIG. 4A, the direction of the eyeball 10 is a direction for which the light emitted from the light-emitting unit 21 passes across the anterior chamber 13 of the eyeball 10.

Thus, upon determining that the direction of the eyeball 10 detected by the detection unit 70 is in the permission range 71, the control unit 40 controls the optical system 20 to start emitting light having the intensity used in measurement from the light-emitting unit 21 or to increase the intensity of the light emitted by the light-emitting unit 21 to the intensity used in measurement.

However, when the direction of the eyeball 10 (the pupil 15) is out of the permission range 71 as illustrated in FIG. 4B, the direction of the eyeball 10 is a direction for which the light emitted from the light-emitting unit 21 may directly reach an unintended portion of the eyeball 10, such as the retina 17 of the eyeball 10.

Thus, upon determining that the direction of the eyeball 10 detected by the detection unit 70 is out of the permission range 71 (is not in the permission range 71), the control unit 40 controls the optical system 20 to prohibit the light-emitting unit 21 from emitting light having the intensity used in measurement or from increasing the intensity of the light to the intensity used in measurement.

Although the light-emitting unit 21 emits light having an intensity that does not cause any undesirably influence even if the light reaches an unintended portion of the eyeball 10, such as the retina 17, in some cases in FIG. 4B, illustration of the optical path 28 of such light is omitted in FIG. 4B. That is, the optical path 28 illustrated in FIG. 4A indicates the state in which the light having the intensity used in measurement is emitted.

As described above, the detection unit 70 observes the eyeball 10 all the time and detects the direction of the eyeball 10.

Upon determining that the direction of the eyeball 10 detected by the detection unit 70 is in the permission range 71, the control unit 40 controls the optical system 20 to cause the light-emitting unit 21 to start emitting light having the intensity used in measurement or to cause the light-emitting unit 21 to increase the intensity of the light to the intensity used in measurement.

Upon determining that the direction of the eyeball 10 detected by the detection unit 70 is out of the permission range 71 (is not in the permission range 71), the control unit 40 controls the optical system 20 to prohibit the light-emitting unit 21 from emitting the light having the intensity used in measurement or from increasing the intensity of the light to the intensity used in measurement.

With such control, a situation where light reaches (illuminates) an unintended portion of the eyeball 10, such as the retina 17, is suppressed when the direction of the eyeball 10 is out of the permission range 71.

When the state in which the direction of the eyeball 10 detected by the detection unit 70 is in the permission range (FIG. 4A) changes to the state in which the direction of the eyeball 10 is out of the permission range 71 (FIG. 4B), the control unit 40 controls the optical system 20 to cause the light-emitting unit 21 to stop emitting the light having the intensity used in measurement or to cause the light-emitting unit 21 to decrease the intensity of the light to an intensity lower than the intensity used in measurement.

With such configuration, a situation where light reaches (illuminates) an unintended portion of the eyeball 10, such as the retina 17, is suppressed when the state in which the direction of the eyeball 10 is in the permission range 71 changes (shifts) to the state in which the direction of the eyeball 10 is out of the permission range 71.

FIGS. 5A and 5B describe control performed by the control unit 40 when the state in which the direction of the eyeball 10 is out of the permission range 71 changes to the state in which the direction of the eyeball 10 is in the permission range 71. Specifically, FIG. 5A illustrates the state in which the direction of the eyeball 10 is out of the permission range 71, and FIG. 5B illustrates the state in which the direction of the eyeball 10 is in the permission range 71. That is, FIGS. 5A and 5B illustrate the states opposite to the states illustrated in FIGS. 4A and 4B.

When the state in which the direction of the eyeball 10 detected by the detection unit 70 is out of the permission range 71 (FIG. 5A) changes to the state in which the direction of the eyeball 10 is in the permission range 71 (FIG. 5B), the control unit 40 controls the optical system 20 to cause the light-emitting unit 21 to start emitting light having the intensity used in measurement, which has been stopped, or to cause the light-emitting unit 21 to increase the intensity of the light, which has been decreased, to the intensity used in measurement.

With such control, a situation where light reaches an unintended portion of the eyeball 10, such as the retina 17, is suppressed when the direction of the eyeball 10 is out of the permission range 71. In addition, when the direction of the eyeball 10 changes to be in the permission range 71, the light-emitting unit 21 is caused to start emitting light having the intensity used in measurement or to increase the intensity of the light, which has been decreased, to the intensity used in measurement. In this way, optical measurement of the eyeball 10 is started.

That is, optical measurement of the eyeball 10 is successfully performed while suppressing a situation where light reaches (illuminates) an unintended portion of the eyeball 10, such as the retina 17, on the basis of the direction of the eyeball 10 detected by the detection unit 70.

The control unit 40 may perform the following control in accordance with FIGS. 4A to 5B.

When the direction of the eyeball 10 detected by the detection unit 70 is in the permission range 71, the control unit 40 causes the light-emitting unit 21 to start emitting light having the intensity used in measurement or to increase the intensity of the light to the intensity used in measurement. When the direction of the eyeball 10 changes to be out of the permission range 71, the control unit 40 causes the light-emitting unit 21 to stop emitting the light having the intensity used in measurement or to decrease the intensity of the light to an intensity lower than the intensity used in measurement. Further, when the direction of the eyeball 10 then changes to be in the permission range 71, the control unit 40 causes the light-emitting unit 21 to start emitting the light having the intensity used in measurement again or to increase the intensity of the light to the intensity used in measurement again.

In addition, stopping emitting light (decreasing the intensity) and restarting emitting light (increasing the intensity) may be repeated further.

Optical Measurement Method

An optical measurement method performed on the eyeball 10 under the control of the control unit 40 will be described below with reference to flowcharts.

Figure 6:
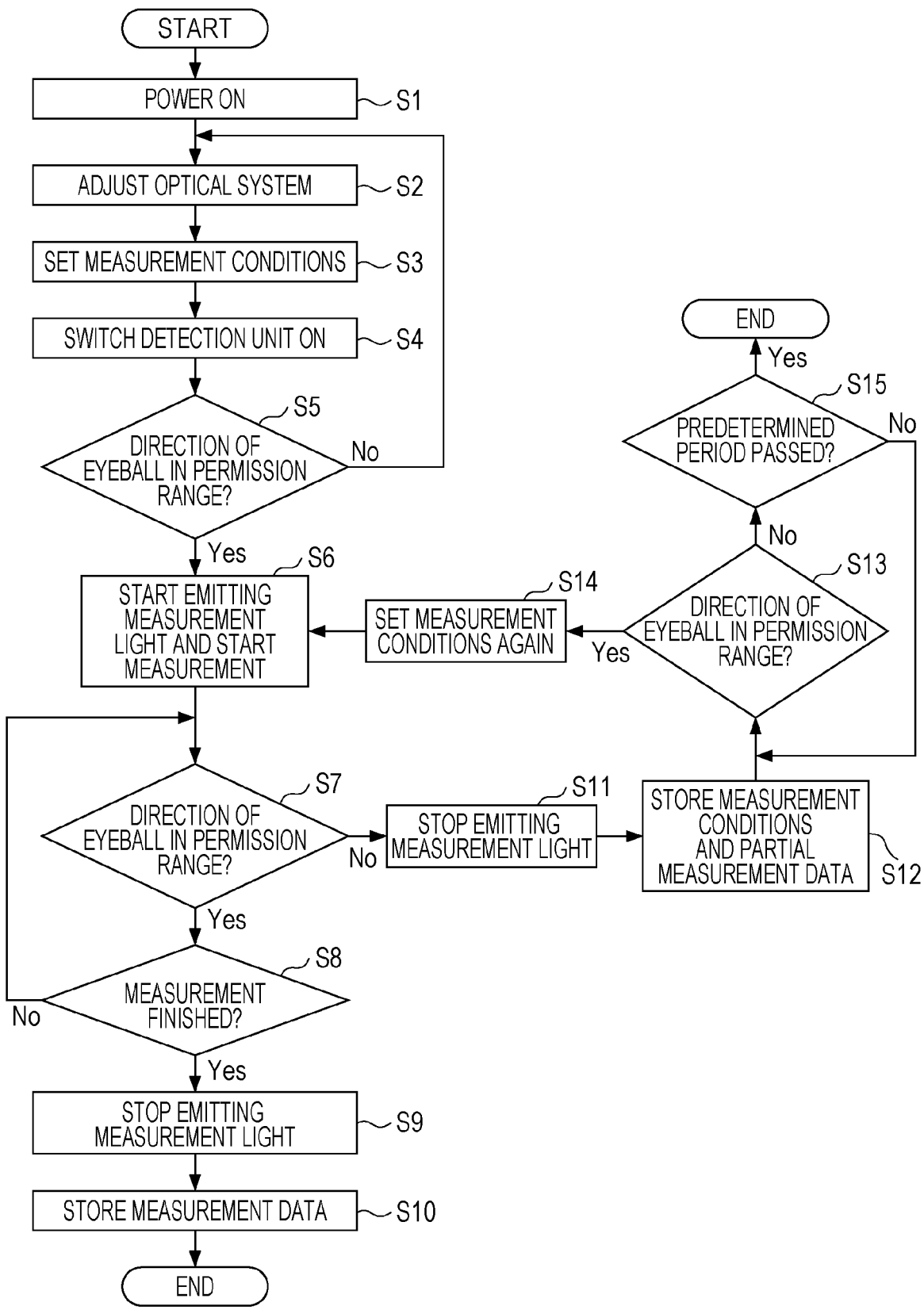
FIG. 6 is an example of a flowchart describing an optical measurement method performed using the optical measurement apparatus.

FIG. 6 is an example of a flowchart describing the optical measurement method performed using the optical measurement apparatus 1.

Hereinafter, "light used in measurement" is referred to as "measurement light", and "causing the light-emitting unit 21 to start emitting light having an intensity used in measurement or to increase the intensity of the light to the intensity used in measurement" is referred to as "starting emitting measurement light (starting emission of measurement light)". In addition, "causing the light-emitting unit 21 to stop emitting the light having the intensity used in measurement or to decrease the intensity of the light emitted by the light-emitting unit 21 to an intensity lower than the intensity used in measurement to an intensity that does not cause any undesirably influence even if the light reaches an unintended portion of the eyeball 10, such as the retina 17" is referred to as "stopping emitting measurement light (stopping emission of measurement light)".

The holding unit 50 of the optical measurement apparatus 1 is held in the vicinity of the eyeball 10 of the subject. Then, the subject or another person powers on the optical measurement apparatus 1 (step 1, which is denoted as S1 in FIG. 6, and the same applies to other steps).

Consequently, the marking (line-of-sight target) 31 is displayed on the display unit 30, and the eyeball 10 of the subject is directed toward the marking (line-of-sight target) 31. This state is a state in which light emitted from the light-emitting unit 21 may transmit across the anterior chamber 13 of the eyeball 10 according to the optical path 28. Thus, the direction of the eyeball 10 is estimated to be in the permission range 71 in this state.

Then, the optical system 20 is adjusted (step 2).

Specifically, the optical system 20 (the light-emitting system 20A and the light-receiving system 20B) is adjusted to set the optical path 28 by using weak light having an intensity that does not cause any undesirable influence even if an unintended portion of the eyeball 10, such as the retina 17, is illuminated by the light, such that the light emitted from the light-emitting unit 21 transmits across the anterior chamber 13 of the eyeball 10. Note that the weak light may be light that has a wavelength used in measurement but has an intensity lower than the intensity used in measurement or weak light that has a wavelength different from the wavelength used in measurement and is easily visible.

Then, measurement conditions are set (step 3).

Examples of the measurement conditions include the type (wavelength) of light used in measurement, the polarization state of the light used in measurement, and duration of measurement. As described above, the order in which multiple light beams having different wavelengths are emitted may be set.

Thereafter, the detection unit 70 is switched on (step 4).

Then, the control unit 40 determines whether the direction of the eyeball 10 detected by the detection unit 70 is in the permission range 71 (step 5).

Step 5 is a step of detecting the direction of the eyeball 10.

If Yes is determined by the control unit 40 in step 5, that is, if it is determined that the direction of the eyeball 10 is in the permission range 71, the control unit 40 controls the light-emitting unit 21 to start emitting the measurement light and starts measurement (step 6). Step 6 is a step of starting emitting light having the intensity used in measurement or increasing the intensity of the light to the intensity used in measurement and of receiving the light used in measurement.

If No is determined by the control unit 40 in step 5, that is, if it is determined that the direction of the eyeball 10 is out of the permission range 71, the process returns to step 2 of adjusting the optical system 20.

This case corresponds to the case where the positional relationship between the direction of the eyeball 10 detected by the detection unit 70 and the optical system 20 is shifted from each other. Specifically, this case corresponds to the case where the direction of the eyeball 10 detected by the detection unit 70 is not in the permission range 71 even if the optical path 28 is set such that the light emitted by the light-emitting unit 21 transmits across the anterior chamber 13 of the eyeball 10 in step 2 of adjusting the optical system 20. Thus, the optical system 20 is adjusted again.

The control unit 40 determines whether the direction of the eyeball 10 is in the permission range 71 (step 7) in a state in which the measurement light is emitted from the light-emitting unit 21 in step 6.

If Yes is determined by the control unit 40 in step 7, that is, if it is determined that the direction of the eyeball 10 (the pupil 15) is in the permission range 71, the control unit 40 determines whether the measurement is finished (step 8).

The case where No is determined by the control unit 40 in step 7 will be described later.

If Yes is determined by the control unit 40 in step 8, that is, if it is determined that the measurement is finished, the control unit 40 controls the light-emitting unit 21 to stop emitting the measurement light (step 9).

Then, the control unit 40 stores an output signal corresponding to the intensity of the light received by the light-receiving unit 27 in a memory included in the control unit 40 as measurement data (step 10).

In this way, the measurement ends. Thereafter, the control unit 40 sends the measurement data to the calculation unit 60. The control unit 40 receives, for example, a concentration of an optically active substance determined as a result of the calculation unit 60 performing calculation based on the measurement data and displays the concentration of the optically active substance on the display unit 30.

On the other hand, if No is determined by the control unit 40 in step 7, that is, if it is determined that the direction of the eyeball 10 is out of the permission range 71, the control unit 40 controls the light-emitting unit 21 to stop emitting the measurement light (step 11). The control unit 40 then stores the measurement conditions and measurement data (partial measurement data) received from the light-receiving unit 27 up to this point (up to the suspension of the measurement) in the memory (step 12).

Then, the control unit 40 determines whether the direction of the eyeball 10 detected by the detection unit 70 is in the permission range 71 (step 13).

If Yes is determined by the control unit 40 in step 13, that is, if it is determined that the direction of the eyeball 10 is in the permission range 71, the control unit 40 sets the measurement conditions again (step 14). The measurement conditions are set again so as to set the measurement conditions for measurement that has not been finished on the basis of the measurement conditions and the partial measurement data stored in the memory.

The process then returns to step 6, in which the light-emitting unit 21 starts emitting the measurement light and measurement is started based on the measurement conditions set again. That is, the measurement is continued from the point at which the measurement has been suspended.

If No is determined by the control unit 40 in step 13, that is, if it is determined that the direction of the eyeball 10 is out of the permission range 71, the control unit 40 determines whether a predetermined period has passed (step 15).

If No is determined by the control unit 40 in step 15, that is, if the predetermined period has not passed, the process returns to step 13, in which the control unit 40 determines whether the direction of the eyeball 10 detected by the detection unit 70 is in the permission range 71.

On the other hand, if Yes is determined by the control unit 40 in step 15, that is, if the predetermined period has passed, the measurement may be finished.

The measurement may be finished because the cornea 14 of the eyeball 10 may dry and, consequently, the state of the eyeball 10 may be unsuitable for measurement.

Note that the measurement conditions set in step 3 may be set again in step 14 without storing the measurement conditions and the partial measurement data in step 12. In this case, the measurement is started over again.

Figure 7:
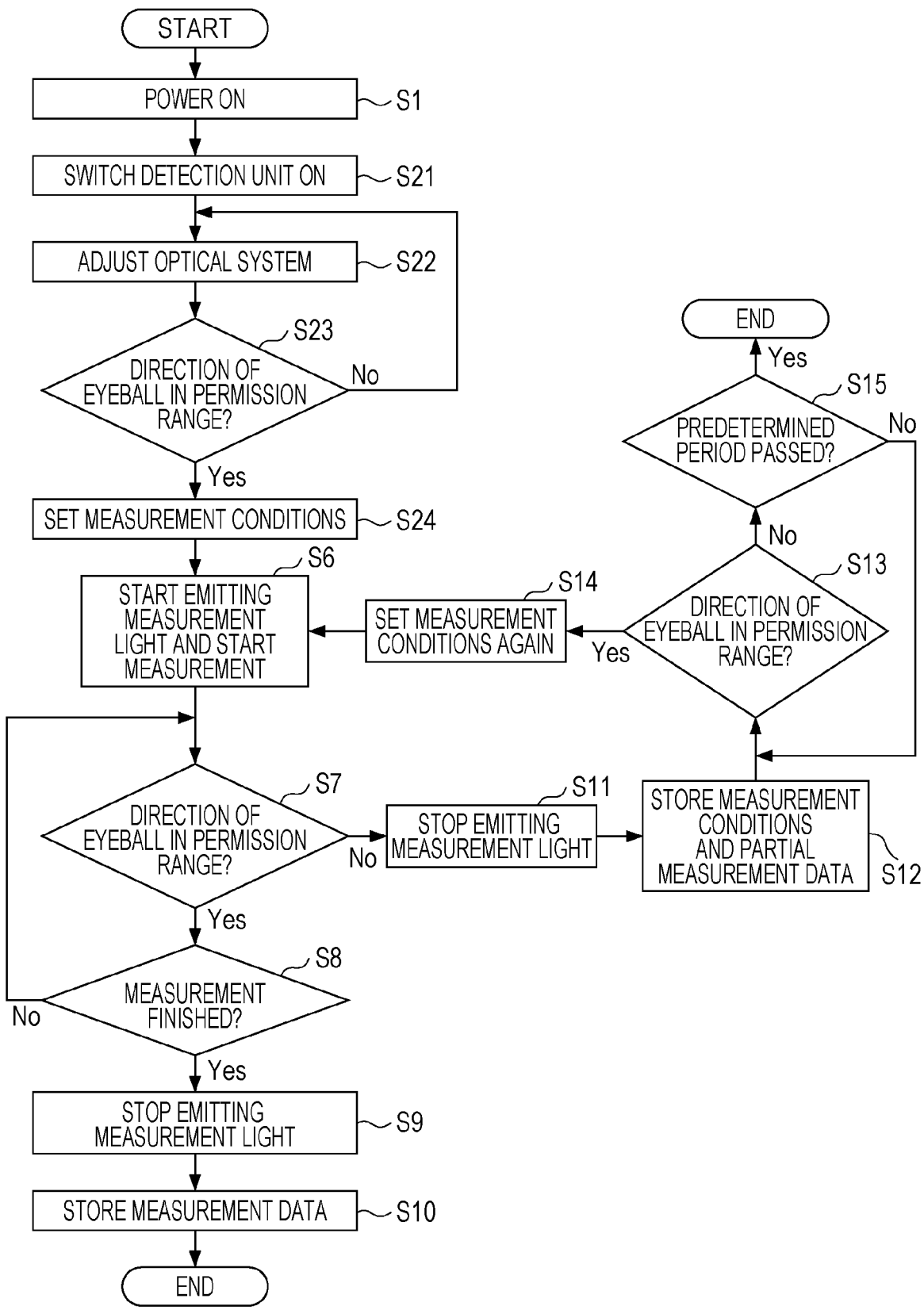
FIG. 7 is an example of a flowchart describing another optical measurement method performed using the optical measurement apparatus.

FIG. 7 is an example of a flowchart describing another optical measurement method performed using the optical measurement apparatus 1.

In FIG. 7, steps that are substantially the same as those of the flowchart illustrated in FIG. 6 are denoted by the same reference signs, and different steps are denoted by different reference signs. That is, steps 2 to 5 of FIG. 6 are changed to steps 21 to 24 in FIG. 7.

Differences will be described below.

After the optical measurement apparatus 1 is powered on in step 1, the detection unit 70 is switched on (step 21).

Then, the optical system 20 is adjusted (step 22). Step 22 is substantially the same as step 2 of FIG. 6.

Then, the control unit 40 determines whether the direction of the eyeball 10 detected by the detection unit 70 is in the permission range 71 (step 23). Step 23 is substantially the same as step 5 of FIG. 6.

If Yes is determined by the control unit 40 in step 23, that is, if it is determined that the direction of the eyeball 10 is in the permission range 71, measurement conditions are set (step 24).

Then, the control unit 40 controls the light-emitting unit 21 to start emitting the measurement light and starts measurement (step 6). Since the following steps are substantially the same as those of the flowchart illustrated in FIG. 6, a description thereof is omitted.

On the other hand, if No is determined by the control unit 40 in step 23, that is, if it is determined that the direction of the eyeball 10 is out of the permission range 71, the process returns to step 22 of adjusting the optical system 20.

As described above, this case corresponds to the case where the positional relationship between the direction of the eyeball 10 detected by the detection unit 70 and the optical system 20 is shifted from each other. Thus, the optical system 20 is adjusted again.

This configuration allows adjustment of the optical system 20 and detection of the direction of the eyeball 10 by the detection unit 70 to be repeated at a short interval, making it easier to set the positional relationship between the direction of the eyeball 10 and the optical system 20 appropriate.

As described above, the state in which the holding unit 50 of the optical measurement apparatus 1 is held in the vicinity of the eyeball 10 of the subject is set such that the light emitted from the light-emitting unit 21 may transmit across the anterior chamber 13 of the eyeball 10 according to the optical path 28. Thus, it is considered that steps 22 and 23 are repeated rarely.

The method for calculating a concentration of a target optically active substance contained in the aqueous humor has been described above as an example of optical measurement performed on the eyeball 10. However, another property of the aqueous humor, for example, light scattering or light absorption may be measured by using transmittance.

The configuration described in the embodiment may be used to determine the properties of the cornea 14 or the like located along the optical path 28 as well as to determine the properties of the aqueous humor. In this case, measurement may be performed by allowing light to transmit across the cornea 14.

That is, the state in which light passes across the eyeball 10 includes not only the state in which the light passes across the anterior chamber 13 but also the state in which the light passes across the cornea 14.

The description is given for the left eye in the embodiment. However, the embodiment may be applied to the right eye.

In addition, the control unit 40 and the calculation unit 60 may be integrated together. Data may be exchanged between the control unit 40 and the calculation unit 60 via a cable or wirelessly.

The foregoing description of the exemplary embodiment of the present invention has been provided for the purposes of illustration and description. It is not intended to be exhaustive or to limit the invention to the precise forms disclosed. Obviously, many modifications and variations will be apparent to practitioners skilled in the art. The embodiment was chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An optical measurement apparatus for an eyeball, comprising:
   a light emitter configured to emit light to pass through an anterior chamber of an eyeball of a subject, in which:
   the eyeball defines a depth direction from a front portion of the eyeball to a back portion of the eyeball of the subject and a width direction perpendicular to the depth direction from an inner corner of the eyeball adjacent a nose of the subject to an outer corner of the eyeball adjacent an ear of the subject, and
   the light emitter emits light in the width direction through the anterior chamber of the eyeball of the subject;
   a polarizer that receives the light emitted from the light emitter and permits linearly polarized light on a predetermined polarization plane to pass therethrough prior to reaching the anterior chamber of the eyeball;
   a compensator configured to receive the light transmitted through the anterior chamber of the eyeball and apply a magnetic field to rotate the light to return the polarization plane that has optically rotated due to transmission through the anterior chamber back to the predetermined polarization plane;
   a light receiver configured to receive light passed through the compensator and output an intensity of the light to the controller;
   a detector configured to detect a direction of the eyeball; and a controller that performs control such that the light emitter starts emitting light having an intensity used in measurement or the light emitter increases an intensity of light emitted by the light emitter to the intensity used in measurement in a case where the direction of the eyeball detected by the detector is in a predetermined range, wherein the predetermined range is a range for which the light emitted from the light emitter passes across the anterior chamber of the eyeball without directly reaching a retina of the eyeball.

2. The optical measurement apparatus for an eyeball according to claim 1, wherein the controller performs control such that the light emitter is prohibited from emitting the light or is prohibited from increasing the intensity of the light emitted by the light emitter to the intensity used in measurement in a case where the direction of the eyeball detected by the detector is not in the predetermined range.

3. The optical measurement apparatus for an eyeball according to claim 1, wherein the controller calculates a concentration of a target optically active substance based on the optical rotation of the light transmitted though the anterior chamber of the eyeball.

4. The optical measurement apparatus for an eyeball according to claim 1, further comprising a first mirror and a second mirror, wherein
the first mirror bends an optical path of the light prior to entering the anterior chamber of the eyeball; and
the second mirror bends an optical path of the light after the light is transmitted through the anterior chamber of the eyeball.

5. The optical measurement apparatus for an eyeball according to claim 1, further comprising an analyzer configured to receive light that passes through the compensator and allow the linearly polarized light on the predetermined polarization plane to pass therethrough prior to entering the light receiver.

6. An optical measurement apparatus for an eyeball, comprising:
a light emitter configured to emit light to pass through an anterior chamber of an eyeball of a subject, in which:
the eyeball defines a depth direction from a front portion of the eyeball to a back portion of the eyeball of the subject and a width direction perpendicular to the depth direction from an inner corner of the eyeball adjacent a nose of the subject to an outer corner of the eyeball adjacent an ear of the subject, and
the light emitter emits light in the width direction through the anterior chamber of the eyeball of the subject;
a polarizer that receives the light emitted from the light emitter and permits linearly polarized light on a predetermined polarization plane to pass therethrough prior to reaching the anterior chamber of the eyeball;
a compensator configured to receive the light transmitted through the anterior chamber of the eyeball and apply a magnetic field to rotate the light to return the polarization plane that has optically rotated due to transmission through the anterior chamber back to the predetermined polarization plane;
a light receiver configured to receive light passed through the compensator and output an intensity of the light to the controller;
a detector configured to detect a direction of the eyeball; and
a controller that performs control such that the light emitter stops emitting light or the light emitter decreases an intensity of light emitted by the light emitter to an intensity lower than an intensity used in measurement in a case where the direction of the eyeball detected by the detector, which has been in a predetermined range, changes to be out of the predetermined range, wherein the predetermined range is a range for which the light emitted from the light emitter passes across the anterior chamber of the eyeball without directly reaching a retina of the eyeball.

7. The optical measurement apparatus for an eyeball according to claim 6, wherein the controller performs control such that the light emitter starts emitting light having the intensity used in measurement or the light emitter increases the intensity of the light emitted by the light emitter to the intensity used in measurement in a case where the direction of the eyeball detected by the detector, which has been out of the predetermined range, changes to be in the predetermined range.

8. The optical measurement apparatus according to claim 7, wherein in a case where measurement that has been started when the direction of the eyeball has been in the predetermined range is still being performed when the direction of the eyeball, which has been in the predetermined range, changes to be out of the predetermined range, the controller continuously performs the measurement from a point in which the eyeball is in the predetermined range to a point in which the eyeball changes to be out of the predetermined range.

9. An optical measurement apparatus for an eyeball, comprising:
light-emitting means for emitting light configured to pass through an anterior chamber of an eyeball of a subject, in which:
the eyeball defines a depth direction from a front portion of the eyeball to a back portion of the eyeball of the subject and a width direction perpendicular to the depth direction from an inner corner of the eyeball adjacent a nose of the subject to an outer corner of the eyeball adjacent an ear of the subject, and
the light-emitting means emits light in the width direction through the anterior chamber of the eyeball of the subject;
polarizing means for receiving the light emitted from the light-emitting means and for permitting linearly polarized light on a predetermined polarization plane to pass therethrough prior to reaching the anterior chamber of the eyeball;
compensating means for receiving the light that has transmitted through the anterior chamber of the eyeball and for applying a magnetic field to rotate the light to return the polarization plane that has optically rotated due to transmission through the anterior chamber back to the predetermined polarization plane;
light-receiving means for receiving the light that has passed through the compensating means and for outputting an intensity of the light to the control means;
detecting means configured to detect a direction of the eyeball; and
control means for performing control such that the light-emitting means starts emitting light having an intensity used in measurement or the light-emitting means increases an intensity of light emitted by the light-emitting means to the intensity used in measurement in a case where the direction of the eyeball detected by the detecting means is in a predetermined range,
wherein the predetermined range is a range for which the light emitted from the light emitting means passes across the anterior chamber of the eyeball without directly reaching a retina of the eyeball.

* * * * *

UNITED STATES PATENT AND TRADEMARK OFFICE
CERTIFICATE OF CORRECTION

PATENT NO. : 11,160,448 B2  
APPLICATION NO. : 15/952247  
DATED : November 2, 2021  
INVENTOR(S) : Kazutaka Takeda et al.

Page 1 of 1

It is certified that error appears in the above-identified patent and that said Letters Patent is hereby corrected as shown below:

On the Title Page

Item (71), after "Applicant:", delete "FUJI BUSINESS INNOVATION CORP." and replace it with "FUJIFILM BUSINESS INNOVATION CORP."

Signed and Sealed this  
First Day of March, 2022

Drew Hirshfeld  
*Performing the Functions and Duties of the*  
*Under Secretary of Commerce for Intellectual Property and*  
*Director of the United States Patent and Trademark Office*